United States Patent
Lermer et al.

(10) Patent No.: US 8,344,866 B2
(45) Date of Patent: Jan. 1, 2013

(54) WARNING SYSTEM FOR A MOTOR VEHICLE

(75) Inventors: Ramona Lermer, Munich (DE); Josef Schumann, Munich (DE); Olaf Mueller, Emmering (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 469 days.

(21) Appl. No.: 12/614,188

(22) Filed: Nov. 6, 2009

(65) Prior Publication Data

US 2010/0117814 A1     May 13, 2010

(30) Foreign Application Priority Data

Nov. 7, 2008 (DE) .................. 10 2008 056 343

(51) Int. Cl.
  *B60Q 1/00* (2006.01)
  *B60R 22/00* (2006.01)
  *G08B 23/00* (2006.01)
(52) U.S. Cl. ............... 340/439; 701/45; 340/576
(58) Field of Classification Search ......... 340/576, 340/439, 575, 436, 425.5; 701/45, 301
See application file for complete search history.

(56) References Cited

U.S. PATENT DOCUMENTS

| | | | |
|---|---|---|---|
| 4,953,111 A * | 8/1990 | Yamamoto et al. | 340/575 |
| 7,202,792 B2 * | 4/2007 | Zhang et al. | 340/575 |
| 7,423,540 B2 * | 9/2008 | Kisacanin | 340/576 |
| 7,493,215 B2 * | 2/2009 | Tanaka et al. | 701/456 |
| 7,639,146 B2 * | 12/2009 | Baura | 340/573.1 |
| 7,791,491 B2 * | 9/2010 | Johns | 340/576 |
| 7,830,266 B2 * | 11/2010 | Nakagoshi et al. | 340/576 |
| 8,179,243 B2 * | 5/2012 | Chen et al. | 340/438 |
| 2003/0181822 A1 * | 9/2003 | Victor | 600/558 |
| 2009/0021356 A1 * | 1/2009 | Galley et al. | 340/425.5 |

* cited by examiner

*Primary Examiner* — Benjamin C Lee
*Assistant Examiner* — Sigmund Tang
(74) *Attorney, Agent, or Firm* — Crowell & Moring LLP

(57) ABSTRACT

A warning system for a motor vehicle includes sensor devices for detecting a driving situation, a warning device for the output of a warning to a driver of the motor vehicle, a device for detecting the driver's state of attention that includes operating elements of existing vehicle components, and a control device which triggers the warning device as a function of data of the sensor devices and the device for detecting the state of attention. In this warning system, the device for detecting the state of attention infers a reduced degree of driver attention when a total duration of a sequence of several operating actions related to the operating elements exceeds a minimum duration. A conclusion can also be drawn that the degree of driver attention is reduced when operating inputs are triggered that are known a priori as being cognitively demanding, for example, operating a telephone keypad.

20 Claims, 1 Drawing Sheet

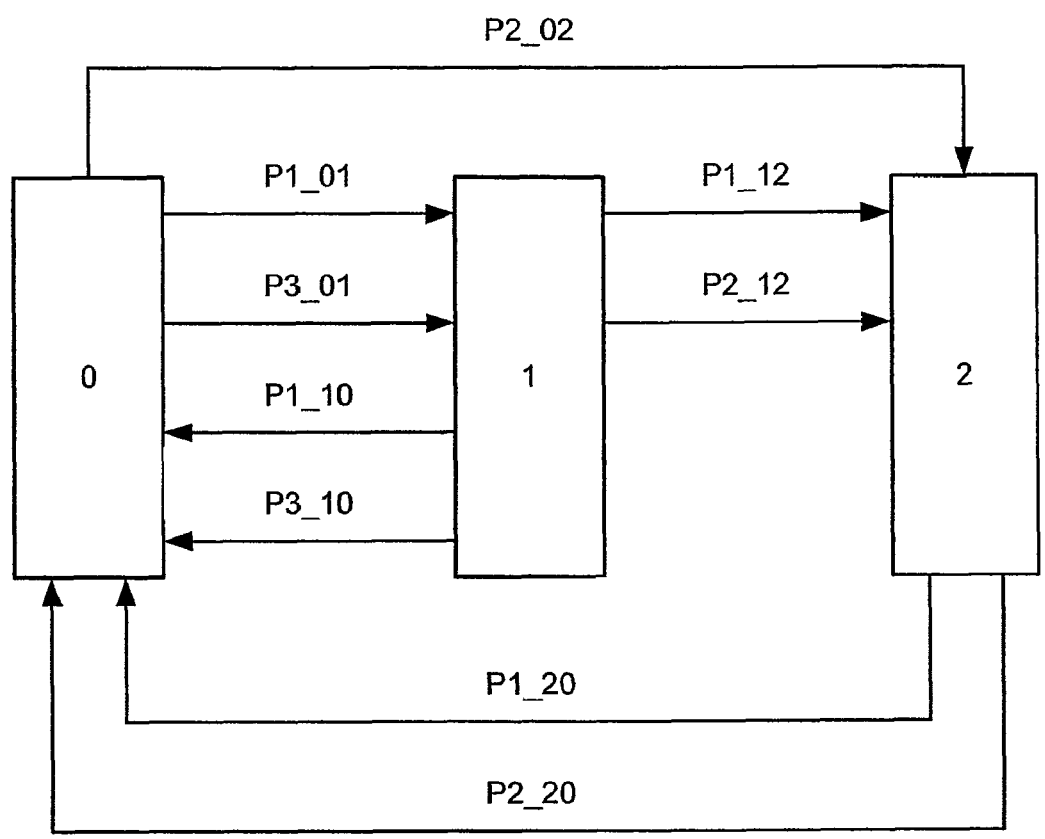

WARNING SYSTEM FOR A MOTOR VEHICLE

CROSS-REFERENCE TO RELATED APPLICATIONS

This application claims priority under 35 U.S.C. §119 to German Patent Application No. DE 10 2008 056 343.9, filed Nov. 7, 2008, the entire disclosure of which is herein expressly incorporated by reference.

BACKGROUND AND SUMMARY OF THE INVENTION

The invention relates to a warning system for a motor vehicle, including sensor devices for detecting a driving situation, a warning device for the output of a warning to a driver of the motor vehicle, a device for detecting the driver's state of attention which includes operating elements of existing vehicle components. The invention also relates to a control device which triggers the warning device as a function of data of the sensor devices and of the device for detecting the state of attention.

Such a warning system is known, for example, from German Patent Document DE 101 63 967 A1. However, the teaching disclosed there discusses only selected aspects that may contribute to reducing the driver's performance. A complete consideration of possible operating actions as one entity is absent.

Further approaches for determining or estimating the degree of a motor vehicle driver's attention provide the high-expenditure sensory detection of the driver's physiological values and/or of his eye movements.

It is an object of the present invention to create a simple warning system in which frequent causes of a reduction of the degree of a motor vehicle driver's attention are taken into account in an improved manner.

This object is achieved by a warning system for a motor vehicle, including sensor devices for detecting a driving situation, a warning device for the output of a warning to a driver of the motor vehicle, a device for detecting the driver's state of attention, which device includes operating elements of existing vehicle components, and a control device which triggers the warning device as a function of data of the sensor devices and of the device for detecting the state of attention. The device for detecting the state of attention infers a degree of a driver's reduced attention when a total duration of a sequence of several operating actions relating to the operating elements exceeds a minimum duration. Advantageous embodiments and further developments of the invention are described herein.

Within the scope of the approach here, the degree of a driver's attention is that fraction of a driver's current overall capability that the driver makes available to his main task, specifically, the task of driving.

Physiological values which, for example, indicate the driver's fatigue or stress, and external influences on the driver are not taken into account within the scope of the present explanations. However, the introduced approach can easily be expanded by taking such quantities into account.

A significant aspect of the approach here consists of drawing conclusions on the driver's degree of attention in that secondary activities are detected which may divert the driver's attention, in that their duration is determined and analyzed and in that their consequences on the driver's degree of attention are estimated. In particular, secondary activities can be detected and considered which consist of operating actions relating to operating elements of the motor vehicle, or secondary activities which go along with such operating actions and are therefore recognizable on the basis of such actions.

In addition to the duration of the secondary activities, advantageous embodiments and further developments of the invention also take into account their type, which is determined or classified by means of the category of the carried-out operating actions.

According to the invention, the device for detecting the state of attention infers a driver's reduced degree of attention when a total time period of a sequence of several operating actions relating to the operating elements of the vehicle exceeds a minimum time period. By providing a minimum time period that has to be exceeded before an impairment of the driver's performance is assumed, several important application situations are excluded in which the assumption of a reduced degree of attention would be unjustified. On the one hand, these include accidentally carried out operating actions and, on the other hand, individual operating actions carried out in a determined manner. The former operating actions are usually carried out accidentally by the driver particularly because he is concentrating on the driving task as a matter of priority. In the case of the latter operating actions, as a rule, the time phase of reduced driver attention will already be concluded with the implementation of the operating action. In these situations, any consequence with respect to the output of warnings by the warning system would be unacceptable for the driver. A time period of 500 ms, for example, would be suitable as a minimum duration.

As a result of the construction of the operating elements in modern vehicles and because of the nature of the usual modes of interaction with such operating elements, an actual operating action, for example, the pressing of a push button or the rotating of a rotating actuator about a lock-in position usually lasts only for a very short time period. With respect to the equipment, such operating actions can often be detected only as time-discrete events of an imperceptible duration. In order to nevertheless assign a duration to a sequence of several operating actions, the total duration of a sequence of several operating actions is preferably determined as the duration of an operating time period in which the time interval between detectable operating actions does not exceed a maximal interruption time duration. For this purpose, the maximal interruption time duration has to be defined to be shorter that the minimum time duration (for example, 300 ms). This approach is capable of changing a sequence of individual operating actions of an imperceptible (or at least very short) duration to a time continuum. Individual operating actions, which themselves last for a certain time period, can nevertheless be integrated in the simple concept without any problem and without special measures by analyzing a time interval.

For certain operating actions, the maximal interruption time period can advantageously be defined individually.

The above considerations can be continued and advantageously implemented in that the approach is carried out in several stages. That means that the device for detecting the state of attention infers an only slightly reduced degree of the driver's attention when a total duration of a sequence of several operating actions exceeds a first (shorter) minimum duration but is below a second (longer) minimum duration. In contrast, the device for detecting the state of attention infers a considerably reduced degree of the driver's attention when a total duration of a sequence of several operating actions finally also exceeds the second minimum duration. A time period of, for example, 500 ms is suitable as a first minimum duration; a time period of, for example, 2,500 ms is suitable as the second minimum duration. This stage model can be reduced to only one—instead of two—stages. Likewise, more than two, for example, three or four stages may be provided.

The above statements relate particularly to operating actions on operating elements for which, on the one hand, a brief operation as well as a longer-lasting operating sequence can seriously be considered and for which, on the other hand, in the case of a longer operating sequence, a stronger distraction of the driver from the driving task should be assumed. These considerations apply, for example, to the operation of window openers, to the navigation through a list-based menu by means of a central operating element or the operation of steering wheel keys.

In addition, other types or categories of operating actions can be integrated in the introduced concept. For this purpose, the device for detecting the state of attention—as above—will then infer a reduced degree of the driver's attention when a total duration of a sequence of several operating actions exceeds a minimum duration. However, this applies only to operating actions of a first category. In addition, the device for detecting the state of attention—independently of a total duration—infers a reduced degree of the driver's attention also when only a single operating action of a second category takes place. For example, the above-mentioned operating actions (operation of a window opener or steering wheel keys, navigation through a list-based menu) could be assigned to the first category. Correspondingly, operating actions would have to be assigned to the second category which point to secondary activities which in each case—independently of the duration of an operating sequence—infer a diversion of the driver; for example, the alphanumeric input of a navigation destination into a navigation device or the dialing of a telephone number.

To continue the above categorization of operating actions, a third category of operating actions can advantageously be defined which do not influence the degree of attention as defined according to the invention. Thus, operating actions which empirically have a low diversion potential and/or relate to the primary driving task may not be taken into account.

Not all secondary activities, which in each case—independently of the duration of an operating sequence—infer a diversion of the driver to the same degree. While certain operating actions, such as the alphanumeric input of a navigation destination into a navigation device, always hold a high diversion potential, in the case of other operating actions, for example, in the case of a volume control of a sound output carried out by steering wheel keys, a defined diversion potential should also always be expected—independently of the duration of an operating sequence. However, this diversion potential can be assessed to be relatively low.

While taking into account the diversity of the operating actions of the above-mentioned two categories, the above-described invention can be advantageously further developed in that the device for detecting the state of attention infers a slightly reduced degree of the driver's attention when a total duration of a sequence of several operating actions of a first category exceeds a first minimum duration but is below a second minimum duration which is longer than the first minimum duration and/or when a single operating action of a second category (for example, volume control by use of steering wheel keys) is carried out. In contrast, an extremely reduced degree of the driver's attention is inferred only when a total duration of a sequence of several operating actions of the first category also exceeds the second minimum duration and/or when a single operating action of a third category (for example, an alphanumeric destination input) is carried out. The categories mentioned within the scope of this further development can therefore be briefly categorized by the keywords "diversion depending on the duration" (first category), "always slightly distracting" (second category), and "always slightly more distracting" (third category).

In a practical further development, advantageously a fourth category of operating actions can be defined, which have no influence on the defined degree of attention. Thus, here also, operating actions which empirically have a low distraction potential may not have to be taken into account.

A possible reaction of the warning system to the definition of the degree of the driver's attention consists of the fact that the point-in-time of the output of a warning to be emitted in a certain driving situation is changed as a function of the driver's degree of attention. In particular, a warning—if it requires a time-critical reaction—in the case of a reduced degree of attention, can be emitted earlier than in the case of a normal degree of attention.

However, it may also be advantageous to make a differentiation with respect to the type of warning. Thus at least a first warning to be emitted in a certain driving situation in the case of a reduced degree of attention can be emitted earlier than in the case of a normal degree of attention, whereby the distracted driver is warned earlier. This is useful for safety-critical warnings and/or time-critical warnings. For example, an exiting traffic lane warning device, which normally emits a warning 0.8 seconds before a probable driving over a side line, in the case of a driver's reduced attention, can emit this warning already one second before the probable driving over the side line. However, at least a second warning to be emitted in a certain driving situation, in the case of a reduced degree of attention, can also be emitted later than in the case of a normal degree of attention or even does not have to be emitted at all. A later output or the omission of an output is useful for non-safety-critical and/or non-time-critical warnings by which the driver would only be distracted further and/or which could further extend the duration of his secondary activity and/or which the already distracted driver could find bothersome.

The introduced approach can advantageously be further developed with respect to leaving a state in which a degree of the driver's reduced attention is assumed. Such a condition can be left again in an event-controlled or time-controlled manner.

On the one hand, after the expiration of an operating time period, in which the time interval between detectable operating actions has not exceeded a maximal interruption time duration and which has lasted so long that a reduced driver attention was assumed within the operating time period, the device for detecting the state of attention immediately can again assume a normal degree of the driver's attention. The return to the normal state will then take place precisely offset by the maximal interruption time period with respect to the last operating action which was to be assigned to the operating sequence.

As mentioned above, the maximal interruption time period can advantageously be defined individually for certain operating actions. However, it can also be defined identically for all operating actions of a category, which simplifies the implementation of the introduced concept.

As an alternative, the device for detecting the state of attention can continue to infer a reduced state of attention within an aftereffect time period after the expiration of such an operating time period and only infer a normal state of attention after the expiration of the aftereffect time period. As a result, the circumstance is taken into account that a driver's full attention as a rule will not be restored immediately after the termination of an operating sequence but that the distraction caused by the operating sequence has an aftereffect.

Particularly when a state was reached in which a reduced degree of the driver's attention was assumed because of operating actions of a category which immediately—independently of the duration of an operating sequence—permit the conclusion that a reduced degree of attention exists (for example, the dialing of a telephone number), the state in which a reduced degree of the driver's attention is assumed can be left or resolved by the detection of a terminating or resolving operating action (for example, terminating the telephone conversation by hanging up).

If no such terminating or resolving operating action exists, a return logic can be used which corresponds to the one that is used when the state of reduced attention was reached by exceeding a minimum duration. Thus, also for the operating actions—which are analyzed independently of the duration per se—and which always permit the inference of a reduced degree of attention, a continuous operating time period is determined in that it is checked whether the interval between detectable operating actions does not exceed a maximal interruption time period. When the maximal interruption time period is exceeded, the operating time period is terminated and a change to the normal condition takes place—possibly delayed by an aftereffect time period.

The estimated value of the driver's state of attention determined according to the invention can be advantageously used in a motor vehicle in multiple manners. According to a preferred embodiment of the present invention, the state of attention is therefore also passed on to other warning systems of the vehicle.

The device for detecting the state of the driver's attention can be constructed to be integrated in the equipment of a certain warning system and can be aimed especially at supporting a certain warning function and can be developed for this warning function. However, the device for detecting the state of attention can also be constructed in a functionally overlapping manner as an autonomous motor vehicle device and/or as part of a higher-ranking warning and information management system. With respect to the equipment, the device for detecting the driver's state of attention may particularly be integrated in the so-called head unit of the motor vehicle or in the so-called front electronic module (FEM).

In the following, a preferred embodiment of the invention will be described by way of a single attached drawing. This embodiment contains further details, preferred types of implementation and further developments of the invention.

BRIEF DESCRIPTION OF THE DRAWING

FIG. 1 is a view of a state transition diagram for reaching various detection states of a device for estimating the driver's performance.

DETAILED DESCRIPTION OF THE DRAWING

An exiting traffic lane warning system for a motor vehicle includes sensor devices (particularly a camera with an image processing device on the output side) for detecting a driving situation and a warning device for the output of a warning to a driver of the motor vehicle. Normally, an acoustic, haptic, and/or visual warning to the driver of the vehicle is emitted 0.8 seconds before a side line limiting a traffic lane will probably be crossed.

The exiting traffic lane warning system includes a control device which triggers the warning device as a function of camera data. The warning point-in-time (normally 0.8 seconds before driving over the side line) can, however, be modified as a function of an estimated degree of attention of the driver of the motor vehicle. In particular, the warning point in time is advanced (for example, 1 second or 1.2 seconds before driving over the side line) when the estimated degree of attention is reduced with respect to a normal state.

A device for detecting the driver's state of attention or the probably available driver performance carries out the estimation of the degree of attention. This device—abbreviated as "a driver performance estimator"—includes operating elements of existing vehicle components of the motor vehicle. The operating actions carried out on these operating elements are detected in different manners and are used for estimating the degree of attention.

FIG. 1 is a view of a state transition diagram for reaching different detection conditions of the driver performance estimator. Here, a differentiation is made between two stages of the reduction of the degree of the driver's attention.

In Stage 1, the driver's attention is slightly (or somewhat) limited. The warning point-in-time of the exiting traffic lane warning system is advanced slightly (here, for example, 1 second before crossing the side line). A visual and/or acoustic warning is emitted.

In Stage 2, the driver's attention is severely limited (or at least more limited than in Stage 1). The warning point-in-time of the exiting traffic lane warning system is advanced even more (here, for example, 1.2 seconds before the vehicle drives over the side line). In addition to the visual and/or acoustic warning, a haptically perceptible warning is emitted.

Stage 0 characterizes the normal state in which the driver's state of attention is not (recognizably) reduced.

FIG. 1 illustrates Stages 0, 1 and 2 and, in addition, by use of transition arrows, shows which transitions are contemplated between Stages 0, 1, 2. The operating actions, by which inferences are made concerning the driver's degree of attention, are divided into a total of four categories.

B0: Operating inputs not analyzed with respect to the estimation of the degree of the driver's attention (for example, setting of a turn signal, operating a start-stop button).

B2: Operating inputs which clearly limit the driver's performance or the degree of the driver's attention—independently of the duration of an individual operating action or of the duration of an operating sequence (for example, start of a telephone conversation, voice input, alphanumeric input of a navigation destination).

B3: Operating inputs which slightly limit the driver's performance or the degree of the driver's attention—independently of the duration of an individual operating action or of the duration of an operating sequence (for example, volume control by use of steering wheel keys).

B1: Operating inputs which limit the driver's performance or the degree of the driver's attention clearly, slightly or not at all as a function of the duration of an operating sequence (for example, actuating of steering wheel keys (with the exception of the volume control), actuating of operating elements of a (possibly range-adaptive) cruise control system, list navigation, actuating of window openers).

Operating actions of Category B0 have no influence on the estimated degree of attention and therefore do not appear in FIG. 1. Starting from Stage 0, operating actions of Category B2 lead to a transition into Stage 2 (see transition arrow P_2_02). Also, starting from Stage 1, operating actions of Category B2 lead to a transition into Stage 2 (see transition arrow P_2_12).

When an operating action is detected which recognizably terminates or resolves the state of reduced attention caused by an operating action of Category B2 (for example, the conclusion of a telephone conversation by hanging up), a transition is made from Stage 2 to Stage 0 (see transition arrow P_2_

20). Likewise, a transition is made from Stage 2 to Stage 0 (also subtotaled under transition arrow P_2_20) when a continuous operating sequence of operating actions of Category B2 (for example, alphanumerical input of a navigation destination or of an address book entry) ends by the exceeding of a maximal interruption duration (for example, 3,000 ms).

Starting from Stage 0, operating actions of Category B3 lead to a transition into Stage 1 (see transition arrow P_3_01). When a continuous operating sequence of operating actions of Category B3 ends by the exceeding of a maximal interruption duration (for example, 1,000 ms), a transition takes place from Stage 1 to Stage 0 (see transition arrow P_3_10).

Whether operating actions of Category B1 result in a stage transition depends on the total duration T of an operating sequence of several operating actions in this category. In this case, the total duration T of a sequence is determined as the duration of an operating time period in which the time interval between detectable operating actions does not exceed a maximal interruption time period (here, 300 ms). When several operating actions of Category B1 (which each are very brief or are to be considered as events of an imperceptible duration) follow one another very closely with respect to time, a continuous operating sequence is assumed. When the total duration T of this operating sequence exceeds a first minimum duration (here, 500 ms) but is still below a second minimum duration (here, 2,500 ms), a transition takes place starting from Stage 0 to Stage 1 (see transition arrow P_1_01). When finally the second minimum duration is also exceeded, a transition takes place from Stage 1 (which previously had necessarily already been reached) to Stage 2 (see transition arrow P_1_12).

When a continuous operating sequence of operating actions of Category B1 ends by the exceeding of the maximal interruption duration (here, 300 ms, see above)—if previously Stage 1 or Stage 2 had been reached because of an operating sequence of operating actions of Category B1—a transition takes place to Stage 0 (see transition arrows P_1_10 and P_1_20).

The above statements relate to an exiting traffic lane warning system having a driver performance estimator. The same driver performance estimator or its output signals can be utilized for additional information, warning, and/or assistance systems of the motor vehicle.

In addition to the change of the timing during the output of warning messages, other conclusions can be drawn from a possibly determined reduction of the degree of the driver's attention or capability and other measures can be taken. In particular, the type, the intensity, and/or the repetition frequency of a warning can be changed as a function of data of the driver performance estimator.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A warning system for a motor vehicle, comprising:
    sensor devices for detecting a driving situation;
    a warning device for output of a warning to a driver of the motor vehicle;
    a device for detecting a driver's state of attention, said driver's state of attention detecting device comprising operating elements of normally existing vehicle components;
    a control device for triggering the warning device as a function of data from the sensor devices and the driver's state of attention detecting device; and
    wherein the driver's state of attention detecting device is operatively configured to infer a degree of a driver's reduced attention when a total duration of a sequence of several operating actions with respect to the operating elements of the normally existing vehicle components exceeds a minimum time duration.

2. The warning system according to claim 1, wherein the total duration of the sequence of several operating actions is determined as a duration of an operating time period in which a time interval between detectable operating actions does not exceed a maximal interruption time duration that is shorter than a minimum time duration.

3. The warning system according to claim 2, wherein the driver's state of attention detecting device is operatively configured to:
    infer a slightly reduced degree of driver attention when the total duration exceeds a first minimum duration but is below a second minimum duration, the second minimum duration being longer than the first minimum duration; and
    infers a severely reduced degree of driver attention when the total duration of the sequence of several operating actions exceeds the second minimum duration.

4. The warning system according to claim 1, wherein the driver's state of attention detection device is operatively configured to:
    infer a reduced degree of driver attention when at least one of:
    (a) the total duration of the sequence of several operating actions categorized into a first category exceeds a minimum duration, and
    (b) a single operating action categorized into a second category occurs.

5. The warning system according to claim 3, wherein the driver's state of attention detection device is operatively configured to:
    infer a reduced degree of driver attention when at least one of:
    (a) the total duration of the sequence of several operating actions categorized into a first category exceeds a minimum duration, and
    (b) a single operating action categorized into a second category occurs.

6. The warning system according to claim 4, wherein operating actions categorized into a third category do not influence an inferred degree of attention.

7. The warning system according to claim 5, wherein operating actions categorized into a third category do not influence an inferred degree of attention.

8. The warning system according to claim 1, wherein the driver's state of attention detection device is operatively configured to:
    infer a slightly reduced degree of driver's attention when at least one of:
    (a) the total duration of the sequence of several operating actions categorized into a first category exceeds a first minimum duration but is below a second minimum duration longer than the first minimum duration, and
    (b) when a single operating action categorized into a second category occurs; and infer a severely reduced degree of driver attention when at least one of:
  (a) the total duration of the sequence of several operating actions of the first category exceeds the second minimum duration, and
  (b) when a single operating action categorized into a third category occurs.

9. The warning system according to claim 2, wherein the driver's state of attention detection device is operatively configured to:
  infer a slightly reduced degree of driver's attention when at least one of:
  (a) the total duration of the sequence of several operating actions categorized into a first category exceeds a first minimum duration but is below a second minimum duration longer than the first minimum duration, and
  (b) a single operating action categorized into a second category occurs; and
  infer a severely reduced degree of driver attention when at least one of:
  (a) the total duration of the sequence of several operating actions of the first category exceeds the second minimum duration and
  (b) when a single operating action categorized into a third category occurs.

10. The warning system according to claim 8, wherein operating actions categorized into a fourth category have no influence on an inferred degree of attention.

11. The warning system according to claim 9, wherein operating actions categorized into a fourth category have no influence on an inferred degree of attention.

12. The warning system according to claim 1, wherein a point-in-time of the output of the warning from the warning device in a certain driving situation is changed as a function of the inferred degree of attention.

13. The warning system according to claim 2, wherein a point-in-time of the output of the warning from the warning device in a certain driving situation is changed as a function of the inferred degree of attention.

14. The warning system according to claim 3, wherein a point-in-time of the output of the warning from the warning device in a certain driving situation is changed as a function of the inferred degree of attention.

15. The warning system according to claim 12, wherein at least a first warning to be emitted in the certain driving situation is emitted earlier when a reduced degree of attention is inferred than in a case of a normal degree of attention; and
  wherein a second warning to be emitted in the certain driving situation is one of not emitted and emitted at a later point-in-time in a case of a reduced degree of attention than in the case of the normal degree of attention.

16. The warning system according to claim 2, wherein within an aftereffect time period after expiration of an operating time period resulting in an inferred reduced degree of driver attention, the detecting device continues to infer the reduced degree of driver attention and determines a normal degree of attention only after the expiration of the aftereffect time period.

17. A method of operating a warning system in a motor vehicle, the warning system including a driver's state of attention detection device that includes operating elements of existing vehicle components, the method comprising the acts of:
  monitoring a total duration of a sequence of several operating actions with respect to the operating elements of the existing vehicle components;
  determining whether the total duration exceeds a minimum duration; and
  inferring a reduced degree of driver attention when the total duration exceeds the minimum duration.

18. The method according to claim 17, further comprising the act of:
  determining the total duration of the sequence of several operating actions as a duration of an operating time period in which a time interval between detectable operating actions does not exceed a maximal interruption time duration which is shorter than the minimum duration.

19. The method according to claim 18, further comprising the acts of:
  determining a slightly reduced degree of driver attention when the total duration exceeds a first minimum duration but is below a second minimum duration that is longer than the first minimum duration; and
  inferring a greater reduced degree of driver attention when the total duration exceeds the second minimum duration.

20. The method according to claim 18, further comprising the acts of:
  determining a slightly reduced degree of driver attention when at least one of:
  (a) the total duration of the sequence of several operating actions categorized into a first category exceeds a first minimum duration but is below a second minimum duration longer than the first minimum duration; and
  (b) a single operating action categorized into a second category occurs; and
  determining a greatly reduced degree of driver attention when at least one of:
  (a) the total duration of the sequence of several operating actions in the first category exceeds the second minimum duration; and
  (b) a single operating action categorized into a third category occurs.

* * * * *